United States Patent
Adam et al.

(10) Patent No.: US 11,969,747 B2
(45) Date of Patent: Apr. 30, 2024

(54) DEVICE FOR DISPENSING A FLUID PRODUCT

(71) Applicant: APTAR FRANCE SAS, Le Neubourg (FR)

(72) Inventors: Fabien Adam, Aviron (FR); Matthieu Baillet, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 354 days.

(21) Appl. No.: 17/611,282

(22) PCT Filed: May 14, 2020

(86) PCT No.: PCT/FR2020/050797
§ 371 (c)(1),
(2) Date: Nov. 15, 2021

(87) PCT Pub. No.: WO2020/234527
PCT Pub. Date: Nov. 26, 2020

(65) Prior Publication Data
US 2022/0212213 A1 Jul. 7, 2022

(30) Foreign Application Priority Data

May 17, 2019 (FR) .................... FA1905215

(51) Int. Cl.
*B05B 7/04* (2006.01)
*B05B 7/24* (2006.01)
(Continued)

(52) U.S. Cl.
CPC .......... *B05B 7/0408* (2013.01); *B05B 7/2467* (2013.01); *B05B 7/2472* (2013.01); *B05B 9/0838* (2013.01); *B05B 11/0032* (2013.01)

(58) Field of Classification Search
CPC ... B05B 7/0408; B05B 7/2467; B05B 7/2472; B05B 9/0838; B05B 11/0032;
(Continued)

(56) References Cited

U.S. PATENT DOCUMENTS 1,495,924 A * 5/1924 Quale ..................... A61M 5/24
604/232
2,316,095 A * 4/1943 Mead, Jr. .......... A61M 5/31595
604/209

(Continued)

FOREIGN PATENT DOCUMENTS

DE 201 07 507 U1 3/2002
WO 00/47332 A1 8/2000
(Continued)

OTHER PUBLICATIONS

International Search Report for PCT/FR2020/050797 dated Aug. 25, 2020.

(Continued)

*Primary Examiner* — Vishal Pancholi
(74) *Attorney, Agent, or Firm* — Sughrue Mion, PLLC

(57) ABSTRACT

A device for dispensing a fluid product, having a body with a dispensing orifice, two removable reservoirs each containing a single dose of fluid product, a dispensing mechanism, and an actuating mechanism. The reservoirs are closed before the dispensing device is actuated. The body has a mechanism for opening each reservoir and adapted to open the reservoirs during actuation of the device. The reservoirs each form a sealed unit which is separate from said body, each reservoir filled with a respective fluid product and hermetically sealed before installed in the body. The body has a receiving mechanism for lateral installation of the reservoirs in the body.

12 Claims, 2 Drawing Sheets

(51) Int. Cl.
　　　*B05B 9/08*　　　(2006.01)
　　　*B05B 11/00*　　(2023.01)
(58) Field of Classification Search
　　　CPC ...... A61M 5/19; A61M 5/30; A61M 15/0025;
　　　　　　A61M 2005/247; A61M 2205/8281;
　　　　　　A61M 2209/10; A61M 2210/04; A61M
　　　　　　2210/0618; A61M 2210/0625; A61M
　　　　　　2210/0662; A61M 11/007; A61M
　　　　　　15/0003; A61M 15/0028; A61M 15/0036;
　　　　　　A61M 15/004; A61M 15/08; A61M
　　　　　　31/00; A61M 35/003; A61J 1/05; A61J
　　　　　　1/1406; A61J 1/1412; A61J 1/1475
　　　USPC ........................................................ 222/135
　　　See application file for complete search history.

(56) References Cited

U.S. PATENT DOCUMENTS

| | | | | |
|---|---|---|---|---|
| 5,480,390 | A | * | 1/1996 | Hajishoreh ........... A61M 5/348 |
| | | | | 604/263 |
| 5,542,934 | A | * | 8/1996 | Silver .................... A61M 5/19 |
| | | | | 604/232 |
| 7,389,946 | B2 | * | 6/2008 | Bruna ............... A61M 15/0041 |
| | | | | 239/320 |
| 2007/0240712 | A1 | | 10/2007 | Fleming et al. |
| 2019/0015613 | A1 | | 1/2019 | Shahaf et al. |
| 2019/0022316 | A1 | | 1/2019 | Bendix |

FOREIGN PATENT DOCUMENTS

| | | |
|---|---|---|
| WO | 03/082702 A2 | 10/2003 |
| WO | 2004/026379 A1 | 4/2004 |
| WO | 2004/050508 A1 | 6/2004 |
| WO | 2012/160157 A1 | 11/2012 |
| WO | 2016/123110 A1 | 8/2016 |

OTHER PUBLICATIONS

Written Opinion for PCT/FR2020/050797 dated Aug. 25, 2020.
French Search Report for PCT/FR2020/050797 dated Aug. 25, 2020.
International Preliminary Report on Patentability dated Nov. 16 2021 with a Translation of the Written Opinion of the International Searching Authority in Application No. PCT/FR2020/050797.

* cited by examiner

DEVICE FOR DISPENSING A FLUID PRODUCT

CROSS REFERENCE TO RELATED APPLICATIONS

This application is a National Stage of International Application No. PCT/FR2020/050797 filed May 14, 2020, claiming priority based on French Patent Application No. FA1905215 filed May 17, 2019.

The present invention relates to a device for dispensing a fluid product, and more particularly to a device of the "combidose" type, i.e. in which two fluid products are mixed and dispensed simultaneously at the moment of actuation.

Dispensers of the combidose type have been developed for many applications, in particular in the field of pharmacy. Such dispensers are of particular application when dispensing nasally. Such devices generally comprise two separate reservoirs, each containing a different fluid product, the products being mixed before or during dispensing in order to be dispensed together. The reservoirs may each contain a single dose or several doses, depending on the type of device. A disadvantage with devices with multi-dose reservoirs is the need to provide metering means for measuring a dose of each fluid product each time it is actuated. These metering means make the device complicated to manufacture and assemble. In addition, there may be risks of contamination of the fluid products contained in each reservoir, in particular between two actuations. A disadvantage of devices with single-dose reservoirs is that they can be used only once, the entire device having to be thrown away after use.

Moreover, depending on the nature of the fluid products, particularly in the case of medicinal products, the conditions for filling and storing the product may be somewhat restrictive. Thus, many fluid products in the pharmaceuticals field have to be filled in a sterile zone and/or stored in a cold chamber. In existing dispensing devices, the products are generally filled after complete assembly of the device, which implies the use of filling machines which are specially adapted to the devices in question, these machines of course having to be in sterile zones. After filling, the device as a whole has to be stored in a cold room. Given the very high costs of industrial sites with sterile areas and of cold room space, the use of specific filling machines proves to be a drawback from an economic point of view, and the same applies as regards storage in a cold room.

The documents US 2007 240712, WO 03082702 and WO 2004/026379 describe devices of the prior art.

The aim of the present invention is to provide a device for dispensing a fluid product which does not suffer from the disadvantages mentioned above.

Thus, the aim of the present invention is to provide a device for dispensing a fluid product of the combidose type which is reusable.

Another aim of the present invention is to provide a fluid product dispensing device of this type for which the sites and spaces of sterile zones during filling and of cold chambers during storage are minimal.

Another aim of the present invention is to provide a fluid product dispensing device of this type which is simple and inexpensive to manufacture and to assemble, and which is reliable in its use.

The present invention therefore provides a device for dispensing a fluid product, comprising a body provided with a dispensing orifice, two removable reservoirs each containing a single dose of fluid product to be dispensed, dispensing means for dispensing said fluid product contained in said reservoirs, and actuating means for actuating said dispensing means, said reservoirs being closed in a sealed manner before the dispensing device is actuated, the body comprising means for opening each reservoir, said opening means being adapted to open said reservoirs when the device is actuated, said reservoirs each forming a sealed unit which is separate from said body, each reservoir being filled with a respective fluid product and hermetically sealed before it is installed in said body, said body comprising receiving means for lateral installation of said reservoirs in said body, said dispensing means comprising a rod associated with each reservoir, said rods being axially displaceable and cooperating with the second sealed closure of each reservoir, each rod being associated with an actuating spring adapted to axially displace said rods during actuation, said rods being integral with an axial slide extending out of said body, said axial slide being axially displaceable with respect to said body between a loaded position, in which said actuating springs are loaded, and an unloaded position after actuation, the user manually returning said slide to the loaded position after each actuation in order to reload said actuating springs.

Advantageously, said receiving means comprise a window provided for each reservoir in a side wall of said body.

Advantageously, each reservoir comprises a hollow tube, comprising a first proximal axial opening and a second distal axial opening, said first axial opening being plugged by a first sealed closure, and said second axial opening being plugged by a second sealed closure.

Advantageously, said first sealed closure is a membrane.

Advantageously, said second sealed closure is a plug, in particular produced from an elastomer.

Advantageously, each reservoir contains a different fluid product, the two different fluid products being mixed during actuation so as to be dispensed together.

In a variation, each reservoir contains a fluid cleaning product and/or decontaminating product in order to form a cleaning reservoir.

Advantageously, said actuating means comprise a lateral actuation element which can be displaced in a direction which is different from the direction of displacement of said dispensing means.

Advantageously, said means for opening the reservoirs comprise means, such as a needle, for piercing said first sealed closure of each reservoir.

Advantageously, each needle is associated with a needle spring which biases a respective reservoir away from said needle when it is installed in said body.

Advantageously, said body, said dispensing means, said actuating means and said opening means are assembled in order to form a unit, said reservoirs being installed in said unit after filling and plugging.

Advantageously, said receiving means comprise a removable cover.

Other characteristics and advantages of the present invention will appear more clearly from the following detailed description, given by way of non-limiting example, and made with reference to the accompanying drawings, in which.

Figure 1:
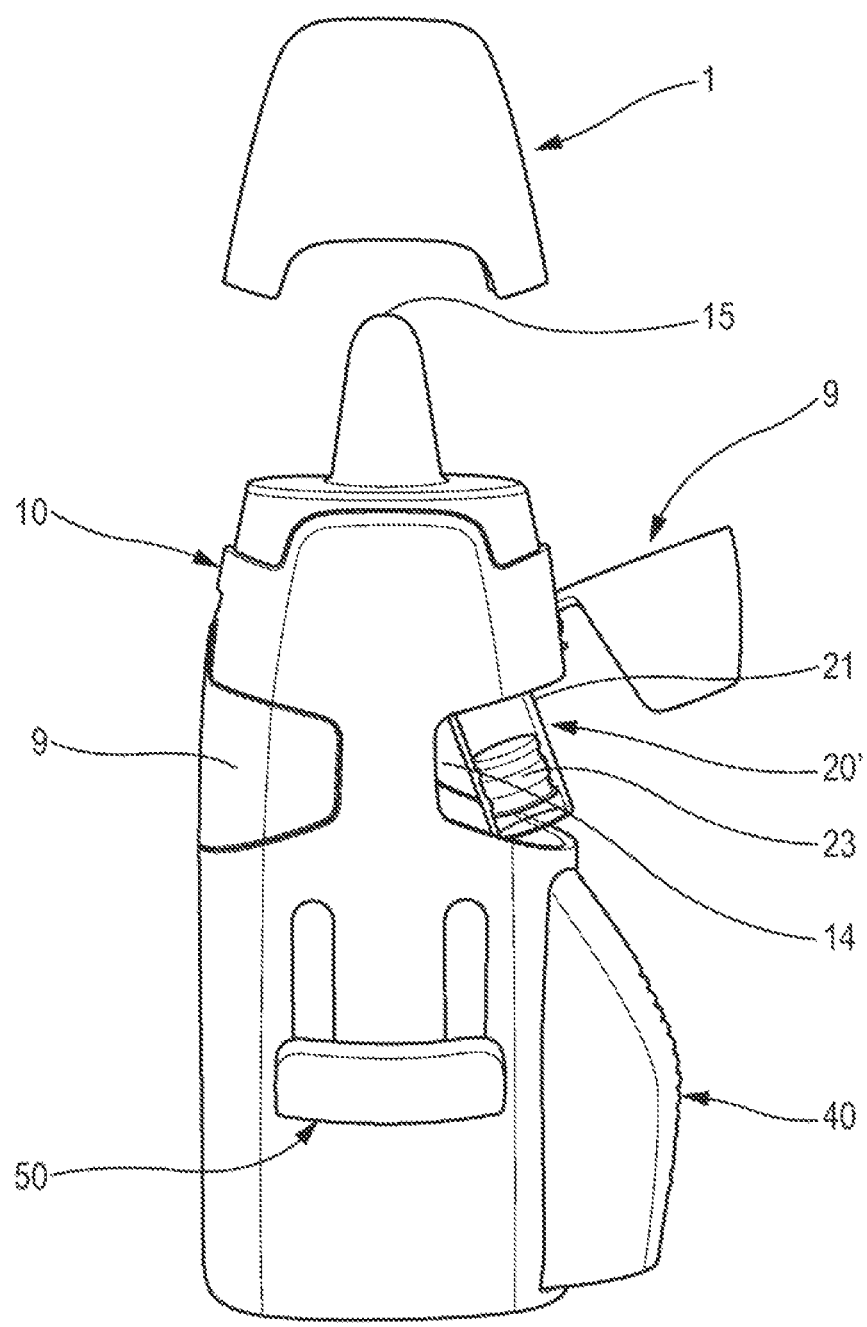
FIG. 1 is a diagrammatic perspective view of a fluid product dispensing device in accordance with an advantageous embodiment.
Figure 2:
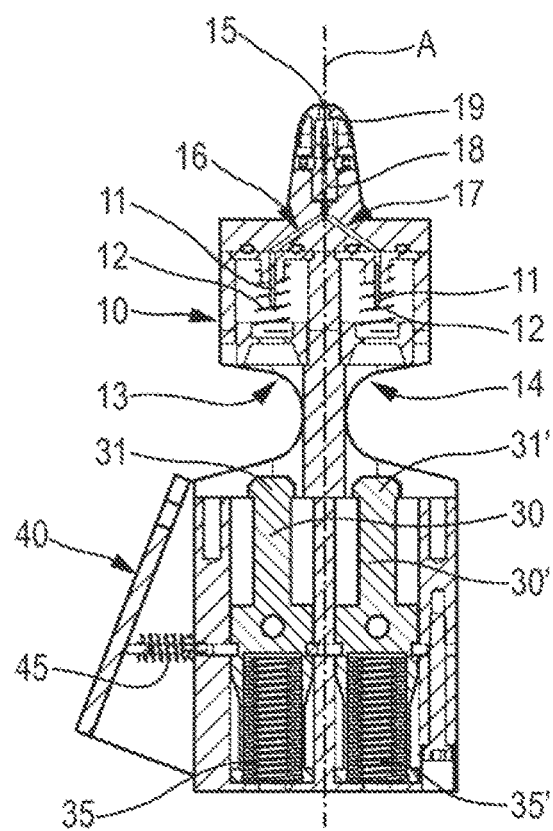
FIG. 2 is a diagrammatic cross-sectional view of a fluid product dispensing device in accordance with an advantageous embodiment, before insertion of the reservoirs.
Figure 3:
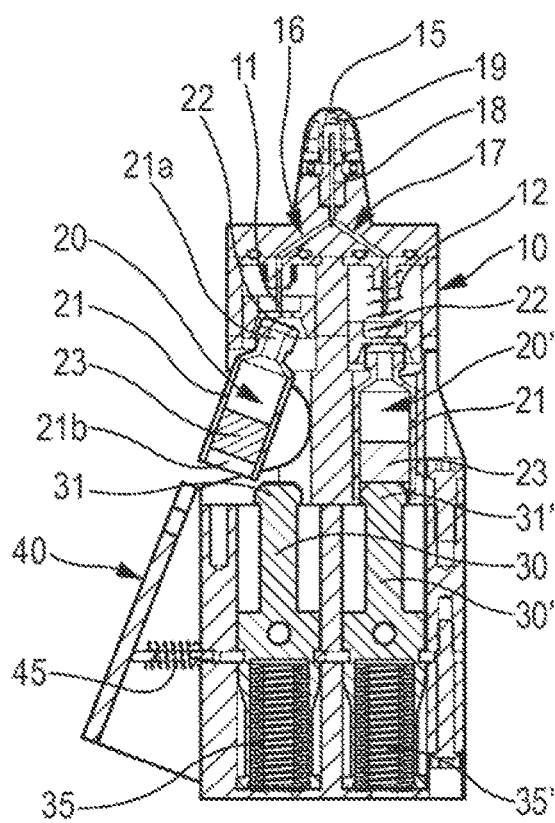
FIG. 3 is a view similar to that of FIG. 2, with one reservoir being secured inside the device and the other reservoir during the course of being inserted.
Figure 4:
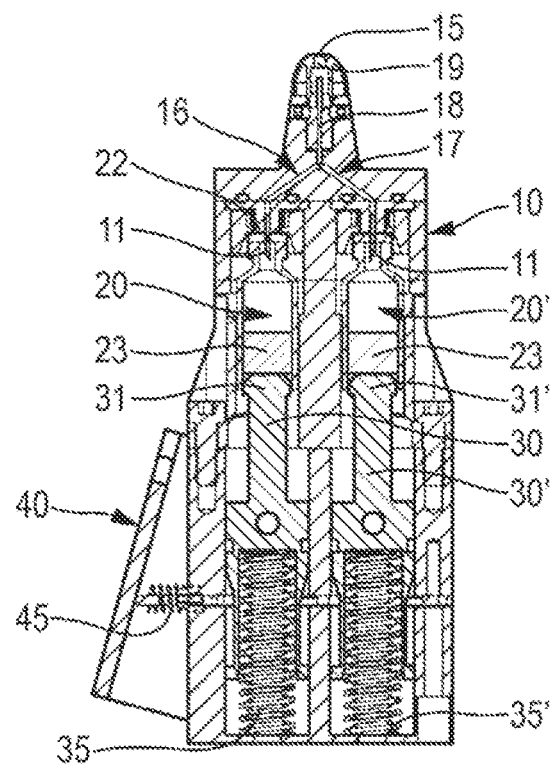
FIG. 4 is a view similar to that of FIG. 3, upon initial actuation of the device.
Figure 5:
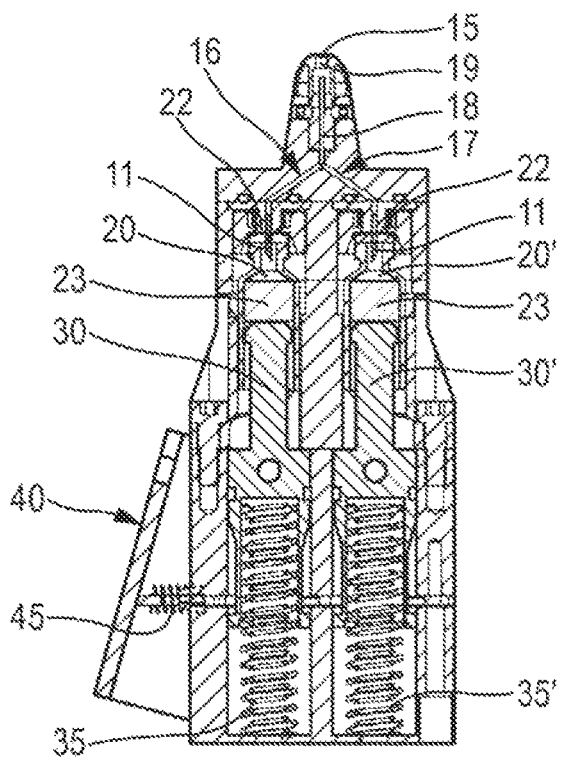
FIG. 5 is a view similar to that of FIG. 4, at the end of actuation of the device.

In the description, the terms "top", "bottom", "upwards", and "downwards" are with respect to the upright position of the device shown in FIGS. 1 to 5. The terms "axial" and "radial" refer to the central vertical axis A of the pump, shown in FIG. 2. The terms "proximal" and "distal" are with respect to the dispensing orifice.

The figures show a combidose type dispensing device. This device comprises a body 10 which is provided with a dispensing orifice 15. In the example shown, the dispensing orifice 15 is formed at the axial end of a nasal dispensing head, which is the preferred embodiment of the invention. It should be noted, however, that oral, auricular or topical distribution could also be envisaged. A removable protective cap 1, which is visible in FIG. 1, may be provided to protect the dispensing orifice 15 between two actuations. The body 10 receives two reservoirs 20, 20', each containing a single dose of a fluid product. In general, these two fluid products are different, but they could also be identical or similar, for example if cleaning reservoirs are used after each actuation, as will be described below.

The two reservoirs 20, 20' are advantageously identical. A single reservoir will therefore be described in greater detail below. Each reservoir forms a sealed unit which is separate from the rest of the device, and is advantageously constituted by a hollow tube 21 comprising a first axial opening 21a and a second axial opening 21b. The first axial opening 21a may be formed in a neck portion of said hollow tube 21. When the reservoirs are installed in the body 10, the first opening 21a forms the proximal opening and the second axial opening 21b forms the distal opening. The first axial opening 21a is plugged by a first sealed closure 22, and the second axial opening 21b is plugged by a second sealed closure 23. The hollow tube 21 may be produced from glass or any other appropriate material. The first sealed closure 22 may be a membrane and the second sealed closure 23 may be a plug 23, advantageously produced from an elastomeric material. In a variation, the first sealed closure 23 could also be a plug 23, advantageously produced from an elastomeric material.

This type of reservoir, which contains only a single dose of product, has very small dimensions, which limits the sterile zone sites for filling and the cold chamber spaces for storing these reservoirs after they have been filled.

The body 10 comprises opening means 11 associated with each reservoir, it being possible for these means to be formed by piercing means such as needles, for example. Each needle 11 is intended to pierce the first sealed closure 22 of a respective reservoir 20, 20' during actuation of the device. Preferably, each needle 11 is fixed with respect to the body 10 and connected to the dispensing orifice 15 via a respective ejection channel 16, 17. Preferably, as can be seen in the figures, the ejection channels 16, 17 of the two needles 11 meet upstream of the dispensing orifice 15 in order to form a single ejection channel 18 leading to said dispensing orifice 15. Advantageously, and in a manner which is well known, a spray profile 19 is provided directly upstream of said dispensing orifice 15.

The dispensing device furthermore comprises dispensing means 30, 30' and actuating means 40 for actuating said dispensing means. The dispensing means comprise a respective rod 30, 30' for each reservoir 20, 20', said rods being axially displaceable so that, during actuation, each cooperates with the plug 23 of a respective reservoir so as to move it axially inside its respective reservoir. Said plugs 23 are therefore transformed into pistons which will slide in the hollow tubes 21 so as to eject the doses of the two fluid products through the needles 11 in the direction of the dispensing orifice 15. Each rod 30, 30' is associated with a respective actuating spring 35, 35' which is adapted to exert the axial force in order to dispense the contents of the reservoirs 20, 20'. In a variation, it is possible to envisage a single rod 30 associated with a single actuating spring 35, it being possible for said rod to be provided at its proximal end with two parallel branches, each of which would cooperate with a respective reservoir 20, 20'.

In the example shown, the actuating springs 35, 35' are disposed between said body 10 and the distal axial ends of said rods 30, 30'.

Said rods are associated with an axial slide 50 extending outside said body 10, as can be seen in FIG. 1. This axial slide 50 is axially displaceable with respect to said body 10, together with said rods 30, 30', between an unloaded position and a loaded position. Thus, when the user displaces said axial slide 50 downwards towards its loaded position, said actuating springs 35, 35' are loaded. During actuation, the rods 30, 30' together with the axial slide 50 are displaced axially upwardly by said actuating springs 35, 35', returning the axial slide 50 to its unloaded position.

Advantageously, said rods 30, 30' and/or said axial slide 50 comprise means for locking in the loaded position, said locking means being released by the actuating means 40 during actuation of the device. These locking means may, for example, comprise snap fitting means which will lock the rods 30, 30' in the loaded position and which are released when the actuating means 40 are actuated.

Preferably, the actuating means 40 comprise a lateral actuation element, i. e. an element which is displaced in a direction which is different from the direction of displacement of the dispensing means. In the example shown, the lateral actuation element is advantageously a lateral lever 40, which is displaceable, in particular pivotable, with respect to said body 10 between a rest position, visible in FIGS. 1 and 2, and an actuation position, visible in FIGS. 3 and 4. A return spring 45 preferably urges said lateral lever 40 towards its rest position.

Each needle 11 is preferably associated with a respective needle spring 12 which is adapted to cooperate with the first opening 21a of each reservoir so as to urge said reservoir away from the respective needle 11. This makes it possible to guarantee that the reservoirs will be opened by piercing the first sealed closures 22 only during actuation of the device. Obviously, the force of said needle springs 12 is less than the force of said actuating springs 35, 35'.

The body 10 comprises means 13, 14 for receiving the reservoirs which form the lateral access means. These receiving means enable the reservoirs 20, 20' to be loaded laterally into the interior of the body 10. The reservoirs 20, 20' can be installed into the interior of the body 10 just before the device is used. Advantageously, the receiving means 13, 14 each comprise a respective window produced in a lateral wall of the body 10. The figures show a body 10 comprising two diametrically opposed side windows. The receiving means may comprise fastening means, for example snap fitting means, or any other appropriate means, which enable the reservoirs 20, 20' to be retained inside the body 10. In the example shown in the figures, the distal opening 21b of each reservoir will be positioned on the proximal axial end 31, 31' of the rods 30, 30', and will be retained in position by the needle springs 12 which push the reservoirs axially downwards. In this embodiment, the plugs 23 which obstruct the distal openings 21b of the reservoirs are slightly offset inside the hollow bodies 21, in order to allow said proximal axial ends 31, 31' of the rods 30, 30' to penetrate slightly into said hollow bodies. Of course, other complementary securing or abutment means may be provided in order to promote secure fastening of these reservoirs 20, 20' in the body 10. Optionally, a respective removable cover 9 may be provided in the region of the receiving means 13, 14, these covers 9 possibly being produced in any desirable manner. FIG. 1 illustrates a possible embodiment in which the two covers 9 are pivotable on the body 10.

Loading the reservoirs laterally into the body 10 therefore makes it possible to produce separate reservoirs, to fill them and to plug them, then to store them independently of the rest of the dispensing device. In turn, the rest of the device can be assembled in a non-sterile area and stored at a location which is not a cold room. It is only very shortly before the device is used that the reservoirs can be installed in the body 10, the contents of the reservoirs remaining protected by the sealed closures 22, 23 until the device is actuated. Loading the reservoirs laterally has the advantage of being able to use lateral actuation with the dispensing means being displaced axially, and of being able to assemble the entire device independently of the reservoirs. Assembly of the device is simplified, and the device itself is also simplified, in particular by not having to use a room which is generally required for pre-assembling the reservoirs when the latter are to be installed axially inside the body. The present invention thus makes it possible to produce a fluid product dispensing device which is less expensive, which operates reliably, and for which considerable savings can be made during filling and storage.

Operation of the device shown in the drawings is as follows: with the axial lever 50 locked in the loaded position, the user can insert a first reservoir 20 containing a dose of a first fluid product into the body 10 through the window 13 of the body. A second reservoir 20' containing a dose of a second fluid product can then be inserted into the body 10 through the window 14 of the body. The needle springs urge said reservoirs 20, 20' axially downwards, away from the needles 11, in order to guarantee the integrity of the contents of said reservoirs. The device is then ready to be actuated.

The user then presses on the lateral lever 40, which will displace the latter towards its actuation position. This displacement of the lateral lever 40 will release the locking means, and thus the rods 30, 30' will be displaced axially upwardly under the effect of the compressed actuating springs 35, 35'. Since the force required to displace the plugs 23 in the hollow bodies 21 of the reservoirs 20, 20' is greater than the force exerted by the needle springs 12 on the reservoirs 20, 20', the axial displacement of the rods 30, 30' initially brings about the upward axial displacement of the reservoirs 20, 20', causing perforation of the membranes 22 by the needles 11. Next, the plugs 23 are displaced in the reservoirs 20, 20' in order to eject the fluid products contained in the two reservoirs. The two fluid products are therefore expelled simultaneously, each through its respective needle 11, and they will mix in the single ejection channel 18, said mixture then being sprayed through the dispensing orifice 15.

After dispensing the two mixed fluid products, the user returns the axial slide 50 to its loaded position, thereby reloading the actuator springs 35, 35', until the rods 30, 30' and the axial slide 50 are locked in the loaded position by the locking means. The two covers 9 can then be opened and the two empty reservoirs 20, 20' can be withdrawn, for example by pushing them manually axially upwardly against the force of the needle springs 12, in order to disengage the distal opening 21b of each reservoir from the upper end 31, 31' of the rods 30, 30'. After removing the two reservoirs 20, 20' from the body 10, the user can optionally wash or clean the device, and in particular the needles 11 and the dispensing orifice, and then store the device for future use with two fresh, full reservoirs.

Advantageously, cleaning is carried out by means of cleaning reservoirs, identical to the reservoirs 20, 20' but containing a cleaning and/or decontaminating fluid product. This makes it possible to clean the needles 11, the ejection channels 16, 17, 18, the spray profile 19 and the dispensing orifice 15. It is thus ensured that the next use with active products is not polluted by the previous use, thereby in particular avoiding any risk of overdose or incompatibility if the subsequent reservoirs contain different products. The actuation cycle for cleaning of this type is identical to the actuation cycle described above except, of course, that the cleaning fluid is not dispensed into the user's nose, mouth, ears or onto the skin.

In particular, but not exclusively, the present invention can be used to treat Parkinson's disease and Huntington's disease, migraine, nasal vaccination, overdose, or heart attack.

Although the invention has been described with reference to a particular embodiment thereof, it is clear that any modification could be applied thereto by a person skilled in the art, without departing from the scope of the present invention as defined in the accompanying claims.

The invention claimed is:

1. A device for dispensing a fluid product, comprising a body provided with a dispensing orifice, two removable reservoirs each containing a single dose of fluid product to be dispensed, dispensing means for dispensing said fluid products contained in said reservoirs, and actuating means for actuating said dispensing means, said reservoirs being closed in a sealed manner before the dispensing device is actuated, the body comprising means for opening each reservoir, said opening means being adapted to open said reservoirs during actuation of the device, said reservoirs each forming a sealed unit which is separate from said body, each reservoir being filled with a respective fluid product and hermetically sealed before it is installed in said body, said body comprising receiving means for lateral installation of said reservoirs in said body, said dispensing means comprising a rod associated with each reservoir, said rods being axially displaceable and cooperating with the second sealed closure of each reservoir, each rod being associated with an actuating spring which is adapted for axially displacing said rods during actuation, characterized in that said rods are secured to an axial slide extending out of said body, said axial slide being axially displaceable with respect to said body between a loaded position, in which said actuating springs are loaded, and an unloaded position after actuation, the user manually returning said slide to the loaded position after each actuation in order to reload said actuating springs.

2. The device as claimed in claim 1, in which said receiving means comprise a window provided for each reservoir in a side wall of said body.

3. The device as claimed in claim 1, in which each reservoir comprises a hollow tube, comprising a first proximal axial opening and a second distal axial opening, said first axial opening being plugged by a first sealed closure, and said second axial opening being plugged by a second sealed closure.

4. The device as claimed in claim 3, in which said first sealed closure is a membrane.

5. The device as claimed in claim 3, in which said second sealed closure is a plug, especially produced from an elastomer.

6. The device as claimed in claim 1, in which each reservoir contains a different fluid product, the two different fluids being mixed upon actuation in order to be dispensed together.

7. The device as claimed in claim 1, wherein each reservoir contains a fluid cleaning product and/or decontaminating product in order to form a cleaning reservoir.

8. The device as claimed in claim 1, in which said actuation means comprise a lateral actuation element which can be displaced in a direction which is different from the direction of displacement of said dispensing means.

9. The device as claimed in claim 1, in which said reservoir opening means comprise means, such as a needle, for piercing said first sealing closure of each reservoir.

10. The device as claimed in claim 9, in which each needle is associated with a needle spring which biases a respective reservoir away from said needle when it is installed in said body.

11. The device as claimed in claim 1, in which said body, said dispensing means, said actuating means and said opening means are assembled in order to form a unit, said reservoirs being installed in this unit after filling and sealing.

12. The device as claimed in claim 1, in which said receiving means comprise a removable cover.

\* \* \* \* \*